US012778946B2

(12) United States Patent
Tabuteau

(10) Patent No.: US 12,778,946 B2
(45) **Date of Patent: *Nov. 3, 2026**

(54) BUPROPION DOSAGE FORMS WITH REDUCED FOOD AND ALCOHOL DOSING EFFECTS

(71) Applicant: ANTECIP BIOVENTURES II LLC, New York, NY (US)

(72) Inventor: Herriot Tabuteau, New York, NY (US)

(73) Assignee: ANTECIP BIOVENTURES II LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/464,192

(22) Filed: Jan. 29, 2026

(65) Prior Publication Data

US 2026/0151387 A1 Jun. 4, 2026

Related U.S. Application Data

(63) Continuation of application No. 19/207,162, filed on May 13, 2025, now Pat. No. 12,564,587, which is a continuation of application No. 18/333,785, filed on Jun. 13, 2023, now Pat. No. 12,310,961, which is a continuation of application No. 18/157,393, filed on Jan. 20, 2023, now Pat. No. 11,717,518.

(60) Provisional application No. 63/370,771, filed on Aug. 8, 2022, provisional application No. 63/370,590, filed on Aug. 5, 2022, provisional application No. 63/357,521, filed on Jun. 30, 2022.

(51) Int. Cl.

*A61K 9/20* (2006.01)
*A61K 31/138* (2006.01)
*A61K 31/485* (2006.01)

(52) U.S. Cl.

CPC .......... *A61K 31/485* (2013.01); *A61K 9/2027* (2013.01); *A61K 9/2086* (2013.01); *A61K 31/138* (2013.01)

(58) Field of Classification Search

CPC ...... A61K 9/20; A61K 9/2004; A61K 9/2009; A61K 9/2077; A61K 9/2086

See application file for complete search history.

(56) References Cited

U.S. PATENT DOCUMENTS

| | | | |
|---|---|---|---|
| 5,358,970 | A | 10/1994 | Ruff et al. |
| 5,731,000 | A | 3/1998 | Ruff et al. |
| 5,763,493 | A | 6/1998 | Ruff et al. |
| 6,306,436 | B1 | 10/2001 | Chungi et al. |
| 6,780,871 | B2 | 8/2004 | Glick et al. |
| 8,088,786 | B2 | 1/2012 | Mckinney et al. |
| 8,569,328 | B1 | 10/2013 | Tabuteau |
| 9,168,234 | B2 | 10/2015 | Tabuteau |
| 9,198,905 | B2 | 12/2015 | Tabuteau |
| 9,205,083 | B2 | 12/2015 | Tabuteau |
| 9,238,032 | B2 | 1/2016 | Tabuteau |
| 9,278,095 | B2 | 3/2016 | Tabuteau |
| 9,314,462 | B2 | 4/2016 | Tabuteau |
| 9,370,513 | B2 | 6/2016 | Tabuteau |
| 9,375,429 | B2 | 6/2016 | Tabuteau |
| 9,402,843 | B2 | 8/2016 | Tabuteau |
| 9,402,844 | B2 | 8/2016 | Tabuteau |
| 9,408,815 | B2 | 8/2016 | Tabuteau |
| 9,421,176 | B1 | 8/2016 | Tabuteau |
| 9,457,023 | B1 | 10/2016 | Tabuteau |
| 9,457,025 | B2 | 10/2016 | Tabuteau |
| 9,474,731 | B1 | 10/2016 | Tabuteau |
| 9,486,450 | B2 | 11/2016 | Tabuteau |

(Continued)

FOREIGN PATENT DOCUMENTS

| | | | |
|---|---|---|---|
| BR | 102016010170 | A2 | 11/2017 |
| EP | 4183391 | A1 | 5/2023 |

(Continued)

OTHER PUBLICATIONS

Goodnick, Psychotropic drugs and the ECG: focus on the QTc interval, Expert Opinion on Pharmacotherapy, vol. 3, No. 5, p. 479-498, 2002.

International Search Report and Written Opinion, PCT/US2024/046359 mailed on Nov. 28, 2024.

Tabuteau H, et al. "Effect of AXS-05 (Dextromethorphan-Bupropion) in Major Depressive Disorder: A Randomized Double-Blind Controlled Trial" Am J Psychiatry (2022) vol. 179 pp. 490-499. doi: 10.1176/appi.ajp.21080800.

International Preliminary Report on Patentability, PCT/US2023/067062, mailed on Nov. 28, 2024.

International Search Report and Written Opinion, PCT/US2024/043903 mailed on Nov. 28, 2024.

(Continued)

*Primary Examiner* — Micah Paul Young

(74) *Attorney, Agent, or Firm* — PROCOPIO, CORY, HARGREAVES & SAVITCH LLP; Brent Johnson; Yuefen Zhou

(57) ABSTRACT

This disclosure relates to dosage forms comprising bupropion hydrochloride, another salt form of bupropion, or the free base form of bupropion; dextromethorphan hydrobromide, another salt form of dextromethorphan, or the free base form of dextromethorphan, and a polymer. In some embodiments, the dosage form has no significant dose dumping of bupropion in the presence of ethanol in vitro. In some embodiments, the dosage form does not have a food effect for bupropion or dextromethorphan when taken with a high-fat meal in human subjects. Some embodiments include a method of treating a nervous system condition (such as depression, e.g., major depressive disorder, including treatment-resistant depression, agitation associated with Alzheimer's disease (or agitation associated with dementia of the Alzheimer's type), agitation associated with dementia, anxiety (or generalized anxiety disorder), neuropathic pain, or peripheral diabetic neuropathic pain) comprising, administering a dosage form described herein to a human being in need thereof.

20 Claims, 2 Drawing Sheets

(56) References Cited

U.S. PATENT DOCUMENTS

| | | | | |
|---|---|---|---|---|
| 9,700,528 | B2 | 7/2017 | Tabuteau | |
| 9,700,553 | B2 | 7/2017 | Tabuteau | |
| 9,707,191 | B2 | 7/2017 | Tabuteau | |
| 9,763,932 | B2 | 9/2017 | Tabuteau | |
| 9,861,595 | B2 | 1/2018 | Tabuteau | |
| 9,867,819 | B2 | 1/2018 | Tabuteau | |
| 9,968,568 | B2 | 5/2018 | Tabuteau | |
| 10,058,518 | B2 | 8/2018 | Tabuteau | |
| 10,064,857 | B2 | 9/2018 | Tabuteau | |
| 10,080,727 | B2 | 9/2018 | Tabuteau | |
| 10,092,560 | B2 | 10/2018 | Tabuteau | |
| 10,092,561 | B2 | 10/2018 | Tabuteau | |
| 10,105,327 | B2 | 10/2018 | Tabuteau | |
| 10,105,361 | B2 | 10/2018 | Tabuteau | |
| 10,251,879 | B2 | 4/2019 | Tabuteau | |
| 10,463,634 | B2 | 11/2019 | Tabuteau | |
| 10,512,643 | B2 | 12/2019 | Tabuteau | |
| 10,548,857 | B2 | 2/2020 | Tabuteau | |
| 10,596,167 | B2 | 3/2020 | Tabuteau | |
| 10,688,066 | B2 | 6/2020 | Tabuteau | |
| 10,695,304 | B2 | 6/2020 | Tabuteau | |
| 10,772,850 | B2 | 9/2020 | Tabuteau | |
| 10,780,064 | B2 | 9/2020 | Tabuteau | |
| 10,780,066 | B2 | 9/2020 | Tabuteau | |
| 10,786,469 | B2 | 9/2020 | Tabuteau | |
| 10,786,496 | B2 | 9/2020 | Tabuteau | |
| 10,799,497 | B2 | 10/2020 | Tabuteau | |
| 10,806,710 | B2 | 10/2020 | Tabuteau | |
| 10,813,924 | B2 | 10/2020 | Tabuteau | |
| 10,864,209 | B2 | 12/2020 | Tabuteau | |
| 10,874,663 | B2 | 12/2020 | Tabuteau | |
| 10,874,664 | B2 | 12/2020 | Tabuteau | |
| 10,874,665 | B2 | 12/2020 | Tabuteau | |
| 10,881,624 | B2 | 1/2021 | Tabuteau | |
| 10,881,657 | B2 | 1/2021 | Tabuteau | |
| 10,894,046 | B2 | 1/2021 | Tabuteau | |
| 10,894,047 | B2 | 1/2021 | Tabuteau | |
| 10,898,453 | B2 | 1/2021 | Tabuteau | |
| 10,925,842 | B2 | 2/2021 | Tabuteau | |
| 10,933,034 | B2 | 3/2021 | Tabuteau | |
| 10,940,124 | B2 | 3/2021 | Tabuteau | |
| 10,945,973 | B2 | 3/2021 | Tabuteau | |
| 10,966,941 | B2 | 4/2021 | Tabuteau | |
| 10,966,942 | B2 | 4/2021 | Tabuteau | |
| 10,966,974 | B2 | 4/2021 | Tabuteau | |
| 10,980,800 | B2 | 4/2021 | Tabuteau | |
| 11,007,189 | B2 | 5/2021 | Tabuteau | |
| 11,020,389 | B2 | 6/2021 | Tabuteau | |
| 11,058,648 | B2 | 7/2021 | Tabuteau | |
| 11,065,248 | B2 | 7/2021 | Tabuteau | |
| 11,090,300 | B2 | 8/2021 | Tabuteau | |
| 11,096,937 | B2 | 8/2021 | Tabuteau | |
| 11,123,343 | B2 | 9/2021 | Tabuteau | |
| 11,123,344 | B2 | 9/2021 | Tabuteau | |
| 11,129,826 | B2 | 9/2021 | Tabuteau | |
| 11,141,388 | B2 | 10/2021 | Tabuteau | |
| 11,141,416 | B2 | 10/2021 | Tabuteau | |
| 11,147,808 | B2 | 10/2021 | Tabuteau | |
| 11,185,515 | B2 | 11/2021 | Tabuteau | |
| 11,191,739 | B2 | 12/2021 | Tabuteau | |
| 11,197,839 | B2 | 12/2021 | Tabuteau | |
| 11,207,281 | B2 | 12/2021 | Tabuteau | |
| 11,213,521 | B2 | 1/2022 | Tabuteau | |
| 11,229,640 | B2 | 1/2022 | Tabuteau | |
| 11,234,946 | B2 | 2/2022 | Tabuteau | |
| 11,253,491 | B2 | 2/2022 | Tabuteau | |
| 11,253,492 | B2 | 2/2022 | Tabuteau | |
| 11,273,133 | B2 | 3/2022 | Tabuteau | |
| 11,273,134 | B2 | 3/2022 | Tabuteau | |
| 11,285,118 | B2 | 3/2022 | Tabuteau | |
| 11,285,146 | B2 | 3/2022 | Tabuteau | |
| 11,291,638 | B2 | 4/2022 | Tabuteau | |
| 11,291,665 | B2 | 4/2022 | Tabuteau | |
| 11,298,351 | B2 | 4/2022 | Tabuteau | |
| 11,298,352 | B2 | 4/2022 | Tabuteau | |
| 11,311,534 | B2 | 4/2022 | Tabuteau | |
| 11,344,544 | B2 | 5/2022 | Tabuteau | |
| 11,357,744 | B2 | 6/2022 | Tabuteau | |
| 11,364,233 | B2 | 6/2022 | Tabuteau | |
| 11,382,874 | B2 | 7/2022 | Tabuteau | |
| 11,419,867 | B2 | 8/2022 | Tabuteau | |
| 11,426,370 | B2 | 8/2022 | Tabuteau | |
| 11,426,401 | B2 | 8/2022 | Tabuteau | |
| 11,433,067 | B2 | 9/2022 | Tabuteau | |
| 11,439,636 | B1 | 9/2022 | Tabuteau | |
| 11,478,468 | B2 | 10/2022 | Tabuteau | |
| 11,497,721 | B2 | 11/2022 | Tabuteau | |
| 11,510,918 | B2 | 11/2022 | Tabuteau | |
| 11,517,542 | B2 | 12/2022 | Tabuteau | |
| 11,517,543 | B2 | 12/2022 | Tabuteau | |
| 11,517,544 | B2 | 12/2022 | Tabuteau | |
| 11,524,007 | B2 | 12/2022 | Tabuteau | |
| 11,524,008 | B2 | 12/2022 | Tabuteau | |
| 11,534,414 | B2 | 12/2022 | Tabuteau | |
| 11,541,021 | B2 | 1/2023 | Tabuteau | |
| 11,541,048 | B2 | 1/2023 | Tabuteau | |
| 11,571,399 | B2 | 2/2023 | Tabuteau | |
| 11,571,417 | B2 | 2/2023 | Tabuteau | |
| 11,576,877 | B2 | 2/2023 | Tabuteau | |
| 11,576,909 | B2 | 2/2023 | Tabuteau | |
| 11,590,124 | B2 | 2/2023 | Tabuteau | |
| 11,596,627 | B2 | 3/2023 | Tabuteau | |
| 11,617,728 | B2 | 4/2023 | Tabuteau | |
| 11,617,747 | B2 | 4/2023 | Tabuteau | |
| 11,628,149 | B2 | 4/2023 | Tabuteau | |
| 11,660,273 | B2 | 5/2023 | Tabuteau | |
| 11,660,274 | B2 | 5/2023 | Tabuteau | |
| 11,717,518 | B1 | 8/2023 | Tabuteau | |
| 11,730,706 | B1 | 8/2023 | Tabuteau | |
| 11,752,144 | B1 | 9/2023 | Tabuteau | |
| 11,779,579 | B2 | 10/2023 | Tabuteau | |
| 11,839,612 | B1 | 12/2023 | Tabuteau | |
| 11,844,797 | B1 | 12/2023 | Tabuteau | |
| 11,883,373 | B1 | 1/2024 | Tabuteau | |
| 11,896,563 | B2 | 2/2024 | Tabuteau | |
| 11,925,636 | B2 | 3/2024 | Tabuteau | |
| 11,969,421 | B2 | 4/2024 | Tabuteau | |
| 11,986,444 | B2 | 5/2024 | Tabuteau | |
| 12,036,191 | B1 | 7/2024 | Tabuteau | |
| 12,042,473 | B2 | 7/2024 | Tabuteau | |
| 12,109,178 | B2 | 10/2024 | Tabuteau | |
| 12,138,260 | B2 | 11/2024 | Tabuteau | |
| 12,146,889 | B1 | 11/2024 | Tabuteau | |
| 12,156,914 | B2 | 12/2024 | Tabuteau | |
| 12,194,005 | B2 | 1/2025 | Tabuteau | |
| 12,194,006 | B2 | 1/2025 | Tabuteau | |
| 12,194,036 | B2 | 1/2025 | Tabuteau | |
| 12,239,642 | B2 | 3/2025 | Tabuteau | |
| 12,263,161 | B2 | 4/2025 | Tabuteau | |
| 12,310,961 | B2 | 5/2025 | Tabuteau | |
| 12,364,674 | B2 | 7/2025 | Tabuteau | |
| 12,370,154 | B2 | 7/2025 | Tabuteau | |
| 12,377,091 | B2 | 8/2025 | Tabuteau | |
| 12,390,428 | B2 | 8/2025 | Tabuteau | |
| 12,433,884 | B2 | 10/2025 | Tabuteau | |
| 12,447,138 | B2 | 10/2025 | Tabuteau | |
| 12,472,155 | B2 | 11/2025 | Tabuteau | |
| 12,472,156 | B2 | 11/2025 | Tabuteau | |
| 12,472,174 | B2 * | 11/2025 | Tabuteau | A61K 31/138 |
| 12,478,622 | B2 | 11/2025 | Tabuteau | |
| 12,544,345 | B2 | 2/2026 | Tabuteau | |
| 12,564,587 | B2 | 3/2026 | Tabuteau | |
| 12,569,479 | B2 | 3/2026 | Tabuteau | |
| 12,576,078 | B1 | 3/2026 | Tabuteau | |
| 12,599,576 | B2 | 4/2026 | Tabuteau | |
| 2002/0035105 | A1 | 3/2002 | Caruso | |
| 2003/0044462 | A1 | 3/2003 | Subramanian et al. | |
| 2008/0044462 | A1 | 2/2008 | Trumbore et al. | |
| 2010/0040679 | A1 | 2/2010 | Chang | |
| 2010/0291225 | A1 | 11/2010 | Fanda et al. | |
| 2015/0126541 | A1 | 5/2015 | Tabuteau | |
| 2015/0126542 | A1 | 5/2015 | Tabuteau | |
| 2015/0126543 | A1 | 5/2015 | Tabuteau | |
| 2015/0126544 | A1 | 5/2015 | Tabuteau | |

(56) References Cited

U.S. PATENT DOCUMENTS

2015/0133485 A1 5/2015 Tabuteau
2015/0133486 A1 5/2015 Tabuteau
2015/0150830 A1 6/2015 Tabuteau
2015/0157582 A1 6/2015 Tabuteau
2015/0342947 A1 12/2015 Pollard et al.
2016/0008352 A1 1/2016 Tabuteau
2016/0030420 A1 2/2016 Tabuteau
2016/0030421 A1 2/2016 Tabuteau
2016/0128944 A1 5/2016 Chawrai et al.
2016/0128998 A1 5/2016 Tabuteau
2016/0136155 A1 5/2016 Tabuteau
2016/0199321 A1 7/2016 Tabuteau
2016/0228390 A1 8/2016 Tabuteau
2016/0263099 A1 9/2016 Tabuteau
2016/0263100 A1 9/2016 Tabuteau
2016/0317475 A1 11/2016 Tabuteau
2016/0317476 A1 11/2016 Tabuteau
2016/0324807 A1 11/2016 Tabuteau
2016/0339017 A1 11/2016 Tabuteau
2016/0346276 A1 12/2016 Tabuteau
2016/0361305 A1 12/2016 Tabuteau
2016/0375008 A1 12/2016 Tabuteau
2016/0375012 A1 12/2016 Tabuteau
2017/0007558 A1 1/2017 Tabuteau
2017/0014357 A1 1/2017 Tabuteau
2017/0252309 A1 9/2017 Tabuteau
2017/0281617 A1 10/2017 Tabuteau
2017/0304229 A1 10/2017 Tabuteau
2017/0304230 A1 10/2017 Tabuteau
2017/0304298 A1 10/2017 Tabuteau
2017/0354619 A1 12/2017 Tabuteau
2017/0360773 A1 12/2017 Tabuteau
2017/0360774 A1 12/2017 Tabuteau
2017/0360776 A1 12/2017 Tabuteau
2018/0092906 A1 4/2018 Tabuteau
2018/0116980 A1 5/2018 Tabuteau
2018/0133195 A1 5/2018 Tabuteau
2018/0207151 A1 7/2018 Tabuteau
2018/0256518 A1 9/2018 Tabuteau
2018/0360823 A1 12/2018 Tabuteau
2019/0000835 A1 1/2019 Tabuteau
2019/0008800 A1 1/2019 Tabuteau
2019/0008801 A1 1/2019 Tabuteau
2019/0008805 A1 1/2019 Tabuteau
2019/0015407 A1 1/2019 Tabuteau
2019/0083426 A1 3/2019 Tabuteau
2019/0142768 A1 5/2019 Tabuteau
2019/0192450 A1 6/2019 Tabuteau
2019/0192507 A1 6/2019 Tabuteau
2019/0216798 A1 7/2019 Tabuteau
2019/0216800 A1 7/2019 Tabuteau
2019/0216801 A1 7/2019 Tabuteau
2019/0290601 A1 9/2019 Tabuteau
2020/0022929 A1 1/2020 Tabuteau
2020/0093762 A1 3/2020 Tabuteau
2020/0147008 A1 5/2020 Tabuteau
2020/0147075 A1 5/2020 Tabuteau
2020/0206217 A1 7/2020 Tabuteau
2020/0215055 A1 7/2020 Tabuteau
2020/0215056 A1 7/2020 Tabuteau
2020/0215057 A1 7/2020 Tabuteau
2020/0215058 A1 7/2020 Tabuteau
2020/0215059 A1 7/2020 Tabuteau
2020/0222389 A1 7/2020 Tabuteau
2020/0230078 A1 7/2020 Tabuteau
2020/0230129 A1 7/2020 Tabuteau
2020/0230130 A1 7/2020 Tabuteau
2020/0230131 A1 7/2020 Tabuteau
2020/0237751 A1 7/2020 Tabuteau
2020/0237752 A1 7/2020 Tabuteau
2020/0246280 A1 8/2020 Tabuteau
2020/0261431 A1 8/2020 Tabuteau
2020/0297666 A1 9/2020 Tabuteau
2020/0338022 A1 10/2020 Tabuteau
2020/0360310 A1 11/2020 Tabuteau
2020/0397723 A1 12/2020 Tabuteau
2020/0397724 A1 12/2020 Tabuteau
2020/0405664 A1 12/2020 Tabuteau
2021/0000763 A1 1/2021 Tabuteau
2021/0000764 A1 1/2021 Tabuteau
2021/0000765 A1 1/2021 Tabuteau
2021/0000768 A1 1/2021 Tabuteau
2021/0000820 A1 1/2021 Tabuteau
2021/0015768 A1 1/2021 Tabuteau
2021/0015814 A1 1/2021 Tabuteau
2021/0015815 A1 1/2021 Tabuteau
2021/0023075 A1 1/2021 Tabuteau
2021/0023076 A1 1/2021 Tabuteau
2021/0030747 A1 2/2021 Tabuteau
2021/0030749 A1 2/2021 Tabuteau
2021/0030750 A1 2/2021 Tabuteau
2021/0030751 A1 2/2021 Tabuteau
2021/0046067 A1 2/2021 Tabuteau
2021/0052521 A1 2/2021 Tabuteau
2021/0060004 A1 3/2021 Tabuteau
2021/0060005 A1 3/2021 Tabuteau
2021/0069125 A1 3/2021 Tabuteau
2021/0069128 A1 3/2021 Tabuteau
2021/0077428 A1 3/2021 Tabuteau
2021/0077429 A1 3/2021 Tabuteau
2021/0077483 A1 3/2021 Tabuteau
2021/0106546 A1 4/2021 Tabuteau
2021/0177834 A1 6/2021 Tabuteau
2021/0186899 A1 6/2021 Tabuteau
2021/0186900 A1 6/2021 Tabuteau
2021/0186901 A1 6/2021 Tabuteau
2021/0186955 A1 6/2021 Tabuteau
2021/0186956 A1 6/2021 Tabuteau
2021/0196704 A1 7/2021 Tabuteau
2021/0196705 A1 7/2021 Tabuteau
2021/0205239 A1 7/2021 Tabuteau
2021/0205240 A1 7/2021 Tabuteau
2021/0205297 A1 7/2021 Tabuteau
2021/0220293 A1 7/2021 Tabuteau
2021/0220294 A1 7/2021 Tabuteau
2021/0220348 A1 7/2021 Tabuteau
2021/0260054 A1 8/2021 Tabuteau
2021/0267967 A1 9/2021 Tabuteau
2021/0338605 A1 11/2021 Tabuteau
2021/0346370 A1 11/2021 Tabuteau
2021/0361645 A1 11/2021 Tabuteau
2021/0401828 A1 12/2021 Tabuteau
2021/0401829 A1 12/2021 Tabuteau
2021/0401830 A1 12/2021 Tabuteau
2021/0401831 A1 12/2021 Tabuteau
2022/0008363 A1 1/2022 Tabuteau
2022/0071930 A1 3/2022 Tabuteau
2022/0071931 A1 3/2022 Tabuteau
2022/0079892 A1 3/2022 Tabuteau
2022/0096462 A1 3/2022 Tabuteau
2022/0105086 A1 4/2022 Tabuteau
2022/0133655 A1 5/2022 Tabuteau
2022/0142950 A1 5/2022 Tabuteau
2022/0193012 A1 6/2022 Tabuteau
2022/0218631 A1 7/2022 Tabuteau
2022/0218698 A1 7/2022 Tabuteau
2022/0233470 A1 7/2022 Tabuteau
2022/0233474 A1 7/2022 Tabuteau
2022/0233518 A1 7/2022 Tabuteau
2022/0233519 A1 7/2022 Tabuteau
2022/0241220 A1 8/2022 Tabuteau
2022/0241221 A1 8/2022 Tabuteau
2022/0241269 A1 8/2022 Tabuteau
2022/0241270 A1 8/2022 Tabuteau
2022/0265639 A1 8/2022 Tabuteau
2022/0280504 A1 9/2022 Tabuteau
2022/0313689 A1 10/2022 Tabuteau
2022/0323381 A1 10/2022 Tabuteau
2022/0378779 A1 12/2022 Tabuteau
2023/0045675 A1 2/2023 Tabuteau
2023/0096437 A1 3/2023 Tabuteau
2023/0099206 A1 3/2023 Tabuteau
2023/0100008 A1 3/2023 Tabuteau
2023/0100913 A1 3/2023 Tabuteau

(56) References Cited

U.S. PATENT DOCUMENTS

| | | | | |
|---|---|---|---|---|
| 2023/0114111 | A1 | 4/2023 | Tabuteau | |
| 2023/0131854 | A1 | 4/2023 | Tabuteau | |
| 2023/0142244 | A1 | 5/2023 | Tabuteau | |
| 2023/0210843 | A1 | 7/2023 | Tabuteau | |
| 2023/0218550 | A1 | 7/2023 | Tabuteau | |
| 2023/0225995 | A1 | 7/2023 | Tabuteau | |
| 2023/0233491 | A1 | 7/2023 | Tabuteau | |
| 2023/0241010 | A1 | 8/2023 | Tabuteau | |
| 2023/0248668 | A1 | 8/2023 | Tabuteau | |
| 2023/0248669 | A1 | 8/2023 | Tabuteau | |
| 2023/0255905 | A1 | 8/2023 | Tabuteau | |
| 2023/0263750 | A1 | 8/2023 | Tabuteau | |
| 2023/0270740 | A1 | 8/2023 | Tabuteau | |
| 2023/0277478 | A1 | 9/2023 | Tabuteau | |
| 2023/0277479 | A1 | 9/2023 | Tabuteau | |
| 2023/0277480 | A1 | 9/2023 | Tabuteau | |
| 2023/0277481 | A1 | 9/2023 | Tabuteau | |
| 2023/0277504 | A1 | 9/2023 | Tabuteau | |
| 2023/0293456 | A1 | 9/2023 | Tabuteau | |
| 2024/0000770 | A1 | 1/2024 | Tabuteau | |
| 2024/0016797 | A1 | 1/2024 | Tabuteau | |
| 2024/0024309 | A1 | 1/2024 | Tabuteau | |
| 2024/0041862 | A1 | 2/2024 | Tabuteau | |
| 2024/0041863 | A1 | 2/2024 | Tabuteau | |
| 2024/0050383 | A1 | 2/2024 | Tabuteau | |
| 2024/0066025 | A1 | 2/2024 | Tabuteau | |
| 2024/0115524 | A1 | 4/2024 | Tabuteau | |
| 2024/0148719 | A1 | 5/2024 | Tabuteau | |
| 2024/0156751 | A1 | 5/2024 | Tabuteau | |
| 2024/0165104 | A1 | 5/2024 | Tabuteau | |
| 2024/0189302 | A1 | 6/2024 | Tabuteau | |
| 2024/0197656 | A1 | 6/2024 | Tabuteau | |
| 2024/0197720 | A1 | 6/2024 | Tabuteau | |
| 2024/0238276 | A1 | 7/2024 | Tabuteau | |
| 2024/0252451 | A1 | 8/2024 | Tabuteau | |
| 2024/0269130 | A1 | 8/2024 | Tabuteau | |
| 2024/0299319 | A1 | 9/2024 | Tabuteau | |
| 2024/0299320 | A1 | 9/2024 | Tabuteau | |
| 2024/0307408 | A1 | 9/2024 | Tabuteau | |
| 2024/0390297 | A1 | 11/2024 | Tabuteau | |
| 2024/0408040 | A1 | 12/2024 | Tabuteau | |
| 2025/0009754 | A1 | 1/2025 | Tabuteau | |
| 2025/0012821 | A1 | 1/2025 | Tabuteau | |
| 2025/0025458 | A1 | 1/2025 | Tabuteau | |
| 2025/0032432 | A1 | 1/2025 | Tabuteau | |
| 2025/0064797 | A1 | 2/2025 | Tabuteau | |
| 2025/0073188 | A1 | 3/2025 | Tabuteau | |
| 2025/0090521 | A1 | 3/2025 | Tabuteau | |
| 2025/0114349 | A1 * | 4/2025 | Tabuteau | A61K 9/2013 |
| 2025/0177380 | A1 | 6/2025 | Tabuteau | |
| 2025/0186428 | A1 | 6/2025 | Tabuteau | |
| 2025/0241907 | A1 | 7/2025 | Tabuteau | |
| 2025/0262175 | A1 | 8/2025 | Tabuteau | |
| 2025/0268890 | A1 | 8/2025 | Tabuteau | |
| 2025/0268891 | A1 | 8/2025 | Tabuteau | |
| 2025/0281430 | A1 | 9/2025 | Tabuteau | |
| 2025/0302969 | A1 | 10/2025 | Tabuteau | |
| 2025/0319043 | A1 | 10/2025 | Tabuteau | |
| 2025/0325539 | A1 | 10/2025 | Tabuteau | |
| 2025/0332123 | A1 | 10/2025 | Tabuteau | |
| 2025/0339538 | A1 | 11/2025 | Tabuteau | |
| 2025/0345294 | A1 | 11/2025 | Tabuteau | |
| 2025/0367142 | A1 | 12/2025 | Tabuteau | |
| 2026/0041651 | A1 | 2/2026 | Tabuteau | |
| 2026/0048129 | A1 | 2/2026 | Tabuteau | |
| 2026/0053758 | A1 | 2/2026 | Tabuteau | |
| 2026/0060976 | A1 | 3/2026 | Tabuteau | |
| 2026/0097006 | A1 | 4/2026 | Tabuteau | |

FOREIGN PATENT DOCUMENTS

| | | | |
|---|---|---|---|
| KR | 101612197 | B1 | 4/2016 |
| WO | 1998050044 | | 11/1998 |
| WO | 2003086362 | A2 | 10/2003 |
| WO | 2004089873 | A1 | 10/2004 |
| WO | 2009006194 | | 1/2009 |
| WO | 2009050726 | A2 | 4/2009 |
| WO | 2015069809 | A1 | 5/2015 |
| WO | 2016125108 | A1 | 8/2016 |
| WO | 2019165379 | A1 | 8/2019 |
| WO | 2020146412 | A1 | 7/2020 |
| WO | 2021202329 | A1 | 10/2021 |
| WO | 2021202419 | A1 | 10/2021 |
| WO | 2022119981 | A1 | 6/2022 |
| WO | 2023004064 | A1 | 1/2023 |
| WO | 2023019138 | A1 | 2/2023 |
| WO | 2023225511 | A1 | 11/2023 |
| WO | 2024006812 | A1 | 1/2024 |
| WO | 2024006853 | A1 | 1/2024 |
| WO | 2024011138 | A1 | 1/2024 |
| WO | 2024118570 | A1 | 6/2024 |

OTHER PUBLICATIONS

International Preliminary Report on Patentability, PCT/US2023/069286, mailed on Jan. 9, 2025.

International Preliminary Report on Patentability, PCT/US2023/069371, mailed on Jan. 9, 2025.

International Preliminary Report on Patentability, PCT/US2023/069655, mailed on Jan. 16, 2025.

Kotlyar et al., Effect of bupropion on physiological measures of stress in smokers during nicotine withdrawal, Pharmacology Biochemistry and Behavior, vol. 83, Issue 3, Mar. 2006, pp. 370-379. [https://doi.org/10.1016/j.pbb.2006.02.017].

International Search Report and Written Opinion, PCT/US2025/016339 mailed on Apr. 3, 2025.

Surovik, J.; et al. "A case of bupropion-induced Stevens-Johnson syndrome with acute psoriatic exacerbation," J. Drugs Dermatol. Aug. 2010, 9(8), 1010-1012. [Abstract].

Garcia, M.; et al. "Eosinophilia associated with bupropion," Int. J. Clin. Pharm. 2013, 35, 532-534. DOI: 10.1007/s11096-013-9803-y. [Abstract].

Ketenci, M.; et al. "Toxic Twist: A Case of Bupropion Induced Brugada Syndrome," Circulation 2023, 148, 1, Abstract 15984. DOI: 10.1161/circ.148.suppl_1.15984. [Abstract].

Ray, A.K.; et al. "Bupropion-Induced Acute Generalized Exanthematous Pustulosis," Pharmacotherapy 2012, 31(6), 621. DOI: 10.1592/phco.31.6.621. [Abstract].

Akbar, D.; et al. "Dextromethorphan-Bupropion for the Treatment of Depression: A Systematic Review of Efficacy and Safety in Clinical Trials," CNS Drugs 2023, 37(10), 867-881. DOI: 10.1007/s40263-023-01032-5. [Abstract].

Mccarthy B.; et al. "Dextromethorphan-bupropion (Auvelity) for the Treatment of Major Depressive Disorder," Clin. Psychopharmacol. Neurosci. 2023, 21(4), 609-616. DOI: 10.9758/cpn.23.1081.

Axsome Therapeutics, Inc. "A Trial of AXS-05 in Patients With Major Depressive Disorder (GEMINI)," Clinicaltrials.gov, NCT04019704 version 8, Sep. 16, 2022.

International Search Report and Written Opinion of the International Searching Authority for PCT/US25/30642, mailed on Jun. 18, 2025.

Iosifescu D. V. et al.: "Efficacy and Safety of AXS-05 (Dextromethorphan-Bupropion) in Patients With Major Depressive Disorder—A Phase 3 Randomized Clinical Trial (Gemini)", Journal of Clinical Psychiatry, 2022, vol. 83, No. 4, article 21ml4345, 9 pages. [DOI: 10.4088/JCP.21ml4345].

Axsome Therapeutics, Inc.: "A Study to Assess the Efficacy and Safety of AXS-05 in Subjects With Treatment Resistant Major Depressive Disorder (STRIDE-I )", ClinicalTrials.gov, NCT02741791, update of Mar. 24, 2021.

Axsome Therapeutics, Inc.: "Open-Label Safety Study of AXS-05 in Subjects With TRD (EVOLVE)", ClinicalTrials.gov, NCT04634669, update of Mar. 7, 2023.

Bisset, Discontinuation of thioridazine, BMJ, vol. 325, p. 967-968, Oct. 26, 2002, bmj.com. [accessed on Jun. 11, 2025].

Jacobson et al., "AXS-05 in Treatment Resistant Depression (TRD) STRIDE-1 Phase 3 Trial Topline Results", AXSOME Therapeutics, Mar. 30, 2020.

(56) References Cited

OTHER PUBLICATIONS

Montgomery et al., “A New Depression Scale Designed to be Sensitive to Change”, British Journal of Psychiatry, vol. 134, No. 4, Apr. 1, 1979, pp. 382-389. (DOI: 10.1192/bjp.134.4.382).
Nobile et al., “Characteristics and treatment outcome of suicidal depression: Two large naturalistic cohorts of depressed outpatients”, Australian and New Zealand Journal of Psychiatry, vol. 56, No. 4, pp. 347-364, 2022. (DOI: 10.1177/00048674211025697).
Jorge Lopez-Castroman et al., “Suicidal Depressed Patients Respond Less Well To Antidepressants in the Short Term”, Depression and Anxiety, New York, NY, US, vol. 33, No. 6, Feb. 16, 2016, pp. 483-494. (DOI: 10.1002/DA.224 73).
Bartol et al., “Use-dependent drug-induced Brugada pattern caused by bupropion in an adolescent with depression”, Journal of the American College of Cardiology, 77(18_Supplement_I), pp. 2117-2117, 2021.
International Search Report and Written Opinion, PCT/US2025/028224 mailed on Jul. 16, 2025.
Settle, “Tinnitus related to bupropion treatment”, Psychiatry and Clinical Psychopharmacology 2014; 24: Supplement S339-S340.
Jerome, “Bupropion and drug-induced parkinsonism,” The Canadian Journal of Psychiatry, 46(6), pp. 560-561, 2001.
International Search Report and Written Opinion, PCT/US2025/033094 mailed on Aug. 26, 2025.
SPRAVATO (esketamine), Highlights of Prescribing Information, revised Jul. 2020.
NUEDEXTA (dextromethorphan hydrobromide and quinidine sulfate), Highlights of Prescribing Information, revised Dec. 2022.
APLENZIN (bupropion hydrobromide), Highlights of Prescribing Information, revised Mar. 2022.
Tod et al., Quantitative Prediction of Cytochrome P450 (CYP) 2D6-Mediated Drug Interactions, Clinical Pharmacokinetics, 50(8), 519-530, Aug. 2011.
Kotlyar et al., Inhibition of CYP2D6 Activity by Bupropion, Journal of Clinical Psychopharmacology, 25(2), 226-229, Jun. 2005.
Pope et al., Pharmacokinetics of Dextromethorphan after Single or Multiple Dosing in Combination with Quinidine in Extensive and Poor Metabolizers, The Journal of Clinical Pharmacology, 44(10), 1132-1142, Oct. 2004.
Auvelity (dextromethorphan hydrobromide and bupropion hydrochloride), Highlights of Prescribing Information and Medication Guide, issued Dec. 2022.
International Preliminary Report on Patentability, PCT/US2021/061492, mailed on Jun. 15, 2023.
International Search Report and Written Opinion, PCT/US2021/061492 received on Jun. 15, 2023.
International Search Report and Written Opinion, PCT/US2022/012768 received on Jul. 5, 2023.
International Search Report and Written Opinion, PCT/US2023/067062 mailed on Jul. 12, 2023.
Axsome Therapeutics Announces Topline Results of the Stride-1 Phase 3 Trial in Treatment Resistant Depression and Expert Call to Discuss Clinical Implications, Mar. 2020 (retrieved from internet on Jul. 19, 2023). <axsometherapeuticsinc.gcs-web.com/node/9176/pdf>.
Anderson, A.; et al. “Efficacy and Safety of AXS-05, an Oral NMDA Receptor Antagonist with Multimodal Activity, in Major Depressive Disorder: Results of a Phase 2, Double-Blind, Active-Controlled Trial” ASCP Annual Meeting 2019 (retrieved from internet on Jul. 19, 2023). <d3dyybxyjb4kyh.cloudfront.net/pdfs/SOBP+2021+AXS-05+MDD+Poster+FINAL.pdf> (May 2019).
O'Gorman, C; et al. “Rapid Effects of AXS 05, an Oral NMDA Receptor Antagonist, in Major Depressive Disorder: Results from Two Randomized, Double Blind, Controlled Trials” ASCP Annual Meeting 2021 (retrieved from internet on Jul. 19, 2023). <d3dyybxyjb4kyh.cloudfront.net/pdfs/SOBP+2021+AXS-05+MDD+Poster+FINAL.pdf> (Jun. 2021).
O'Gorman, C.; et al. “PMH40 Effects of AXS-05 on Patient Reported Depressive Symptoms in Major Depressive Disorder: Results from the GEMINI Trial” <doi.org/10.1016/j.jval.2021.04.662> (retrieved from internet on Jul. 19, 2023). Value in Health, Jun. 2021, vol. 24, Supplement 1, pp. S135.
O'Gorman, C.; et al. “P246. Rapid Antidepressant Effects and MADRS Core Symptom Improvements With AXS-05, an Oral NMDA Receptor Antagonist, in Major Depressive Disorder: Results From Two Randomized, Double-Blind, Controlled Trials” ACNP 60th Annual Meeting: Poster Abstracts P246 <nature.com/articles/s41386-021-01236-7> (retrieved from internet on Jul. 19, 2023). Neuropsychopharmacol. 46 (Suppl 1), 72-217, Dec. 2021.
International Preliminary Report on Patentability, PCT/US2022/012768, mailed on Jul. 27, 2023.
Nofziger et al., Evaluation of dextromethorphan with select antidepressant therapy for the treatment of depression in the acute care psychiatric setting, Mental Health Clinician, 9(2), 76-81, Mar. 2019.
Update: Bupropion Hydrochloride Extended-Release 300 mg Bioequivalence Studies, FDA, retrieved Mar. 2021.
FDA Draft Guidance on Bupropion Hydrochloride, revised Mar. 2013.
FORFIVO XL (bupropion hydrochloride) extended-release tablets, for oral use, Highlights of Prescribing Information, revised Dec. 2019.
FORFIVO XL (Bupropion HCI) extended-release tablet, NDA 22497, Jan. 25, 2010.
WELLBUTRIN XL (bupropion hydrochloride extended-release), Highlights of Prescribing Information, revised Mar. 2022.
Baker T. E. et al., Human Milk and Plasma Pharmacokinetics of Single-Dose Rimegepant 75mg in Healthy Lactating Women, Breastfeeding Medicine, 17(3), 277-282, 2022.
Berle J. O. et al., Antidepressant Use During Breastfeeding, Current Women's Health Reviews, 7(1), 28-34, Feb. 2011.
Briggs G. G. et al., Excretion of bupropion in breast milk, Annals of Pharmacotherapy, 27(4):431-433, Apr. 1993.
Chad L. et al., Update on antidepressant use during breastfeeding, Canadian Family Physician, 59(6), 633-634, Jun. 2013.
Chaudron L. H. et al., Bupropion and Breastfeeding: A case of a possible Infant Seizure, The Journal of clinical psychiatry, 65(6), 881-882, Jun. 2004.
Davis M. F. et al., Bupropion Levels in Breast Milk for 4 Mother-Infant Pairs: More Answers to Lingering Questions, J. Clin. Psychiatry, 70(2), 297-298, Feb. 2009.
Di Scalea T. L. et al., Antidepressant Medication Use during Breastfeeding, Clinical obstetrics and gynecology, 52(3): 483-497, Sep. 2009.
Dwoskin L. P. et al., Review of the Pharmacology and Clinical Profile of Bupropion, and Antidepressant and Tobacco Use Cessation Agent, CNS Drug Reviews, 12(3-4), 178-207, Sep. 2006.
Gentile S, The safety of newer antidepressants in pregnancy and breastfeeding, Drug Safety, 28(2), 137-152, Feb. 2005. [doi: 10.2165/00002018-200528020-00005. PMID: 15691224.].
Haas J. S. et al., Bupropion in breast milk: an exposure assessment for potential treatment to prevent post-partum tobacco use, Tobacco Control, 13(1), 52-56, Mar. 2004.
Ram D. et al., Antidepressants, anxiolytics, and hypnotics in pregnancy and lactation, Indian J Psychiatry, 57(Suppl 2): S354-S371, Jul. 2015. [doi:10.4103/0019-5545.161504].
Weissman A. M. et al., Pooled Analysis of Antidepressant Levels in Lactating Mothers, Breast Milk, and Nursing Infants, Am J Psychiatry, 161(6), 1066-1078, Jun. 2004.
Horn J. R. et al., Get to Know an Enzyme: CYP2D6, Pharmacy Times, Jul. 2008, retrieved on Aug. 28, 2023.
International Search Report and Written Opinion, PCT/US2023/069286 mailed on Aug. 22, 2023.
International Search Report and Written Opinion, PCT/US2023/069239 mailed on Aug. 28, 2023.
International Search Report and Written Opinion, PCT/US2023/069367 mailed on Aug. 28, 2023.
International Search Report and Written Opinion, PCT/US2023/069655 mailed on Sep. 15, 2023.
International Search Report and Written Opinion, PCT/US2023/069371 mailed on Sep. 26, 2023.
International Search Report and Written Opinion, PCT/US2022/037913 mailed on Sep. 21, 2022.

(56) References Cited

OTHER PUBLICATIONS

Jones A et al., "Early Improvements in Functioning and Quality of Life With AXS-05 in Major Depressive Disorder: Results From the Gemini Trial ," Value in Health, Jun. 2021, vol. 24, abstract No. PHM42, p. S135. DOI:10.1016/j.jval.2021.04.662.
International Search Report and Written Opinion, PCT/US2022/074713 mailed on Sep. 21, 2022.
Axsome Therapeutics, Inc.: "MERIT: A Randomized, Double-blind, Placebo-controlled Study of AXS-05 for Relapse Prevention in Treatment Resistant Depression," ClinicalTrials.gov, NCT04608396 version 2, Mar. 24, 2021.
International Preliminary Report on Patentability, PCT/US2022/037913, issued on Jan. 18, 2024.
International Preliminary Report on Patentability, PCT/US2022/074713, issued on Feb. 22, 2024.
Chinese Pat. No. 202080004041.1 Invalidation Notice and Request issued on Jan. 15, 2024. (English translation included).
Ward K. and Citrome L.: "AXS-05: an investigational treatment for Alzheimer's disease-associated agitation", Expert Opinion on Investigational Drugs, Jul. 6, 2022, vol. 31, issue 8, pp. 773-780, DOI: 10.1080/13543784.2022.2096006.
Defendant TEVA Pharmaceuticals, Inc.'s Invalidity Contentions for U.S. Pat. Nos. 11,752,144, 11,717,518, 11,730,706 and Exhibits A-C dated Apr. 11, 2024.
International Search Report and Written Opinion, PCT/US2025/055432 mailed on Jan. 27, 2026.
International Search Report and Written Opinion, PCT/US2025/053844 mailed on Jan. 30, 2026.
International Preliminary Report on Patentability, PCT/US2024/043903, mailed on Mar. 12, 2026.
International Preliminary Report on Patentability, PCT/US2024/046359, mailed on Mar. 26, 2026.
International Search Report and Written Opinion, PCT/US2025/061679, mailed on Apr. 10, 2026.
International Search Report and Written Opinion, PCT/US2024/058092, mailed on Jan. 24, 2025.

* cited by examiner

BUPROPION DOSAGE FORMS WITH REDUCED FOOD AND ALCOHOL DOSING EFFECTS

CROSS-REFERENCE TO RELATED APPLICATIONS

This application is a continuation of U.S. patent application Ser. No. 19/207,162, filed May 13, 2025; which is a continuation of U.S. patent application Ser. No. 18/333,785, filed Jun. 13, 2023, now U.S. Pat. No. 12,310,961; which is a continuation of U.S. patent application Ser. No. 18/157,393, filed Jan. 20, 2023, now U.S. Pat. No. 11,717,518; which claims priority to U.S. Provisional Pat. App. Nos. 63/357,521, filed Jun. 30, 2022, 63/370,590, filed Aug. 5, 2022, and 63/370,771, filed Aug. 8, 2022; all of which are incorporated by reference herein in their entireties.

FIELD

This disclosure relates to dosage forms containing bupropion, optionally in the presence of dextromethorphan, and use of these dosage forms for various therapeutic purposes.

SUMMARY

This disclosure relates to dosage forms comprising bupropion hydrochloride, another salt form of bupropion, or the free base form of bupropion; dextromethorphan hydrobromide, another salt form of dextromethorphan, or the free base form of bupropion, and a polymer. In some embodiments, the dosage form has no significant dose dumping of bupropion in the presence of ethanol in vitro. In some embodiments, the dosage form does not have a food effect for bupropion when taken with a high-fat meal in human subjects. In some embodiments, the dosage form does not have a food effect for dextromethorphan when taken with a high-fat meal in human subjects.

Some embodiments include a dosage form comprising: 105 mg of bupropion hydrochloride, or a molar equivalent amount of another salt form of bupropion or the free base form of bupropion, 45 mg of dextromethorphan hydrobromide, or a molar equivalent amount of another salt form of dextromethorphan or the free base form of dextromethorphan, and a polymer, wherein the dosage form, in the presence of ethanol in vitro, shows no significant dose dumping of bupropion.

Some embodiments include a method of treating a nervous system condition (such as depression, e.g., major depressive disorder, including treatment-resistant depression, agitation associated with Alzheimer's disease (or agitation associated with dementia of the Alzheimer's type), agitation associated with dementia, anxiety (or generalized anxiety disorder), neuropathic pain, or peripheral diabetic neuropathic pain) comprising administering, once a day or twice a day, a dosage form to a human patient in need thereof, wherein the dosage form comprises 105 mg of bupropion hydrochloride, or a molar equivalent amount of another salt form of bupropion or the free base form of bupropion, 45 mg of dextromethorphan hydrobromide, or a molar equivalent amount of another salt form of dextromethorphan or the free base form of dextromethorphan, and a polymer, and wherein the dosage form, in the presence ethanol in vitro, shows no significant dose dumping of bupropion.

Some embodiments include a method of treating a nervous system condition (such as depression, e.g., major depressive disorder, agitation associated with Alzheimer's disease (or agitation associated with dementia of the Alzheimer's type), agitation associated with dementia, anxiety (or generalized anxiety disorder), neuropathic pain, or peripheral diabetic neuropathic pain) comprising administering, once a day or twice a day, a dosage form to a human patient in need thereof, wherein the dosage form comprises 105 mg of bupropion hydrochloride, or a molar equivalent amount of another salt form of bupropion or the free base form of bupropion, 45 mg of dextromethorphan hydrobromide, or a molar equivalent amount of another salt form of dextromethorphan or the free base form of dextromethorphan, and a polymer, and wherein the patient consumes alcohol on a day that the dosage form is administered.

Some embodiments include a method of treating a nervous system condition (such as depression, e.g., major depressive disorder, agitation associated with Alzheimer's disease (or agitation associated with dementia of the Alzheimer's type), agitation associated with dementia, anxiety (or generalized anxiety disorder), neuropathic pain, or peripheral diabetic neuropathic pain) in a human patient who is consuming alcohol, comprising administering, once a day or twice a day, a dosage form to a human patient in need thereof, and limiting but not discontinuing consumption of alcohol by the human patient, wherein the dosage form comprises 105 mg of bupropion hydrochloride, or a molar equivalent amount of another salt form of bupropion or the free base form of bupropion, 45 mg of dextromethorphan hydrobromide, or a molar equivalent amount of another salt form of dextromethorphan or the free base form of dextromethorphan, and a polymer.

Some embodiments include a method of treating a nervous system condition (such as depression, e.g., major depressive disorder, agitation associated with Alzheimer's disease (or agitation associated with dementia of the Alzheimer's type), agitation associated with dementia, anxiety (or generalized anxiety disorder), neuropathic pain, or peripheral diabetic neuropathic pain) in a human patient who is consuming alcohol, comprising administering, once a day or twice a day, a dosage form to a human patient in need thereof, and reducing but not discontinuing consumption of alcohol by the human patient, wherein the dosage form comprises 105 mg of bupropion hydrochloride, or a molar equivalent amount of another salt form of bupropion or the free base form of bupropion, 45 mg of dextromethorphan hydrobromide, or a molar equivalent amount of another salt form of dextromethorphan or the free base form of dextromethorphan, and a polymer.

Some embodiments include a method of treating a nervous system condition (such as depression, e.g., major depressive disorder, agitation associated with Alzheimer's disease (or agitation associated with dementia of the Alzheimer's type), agitation associated with dementia, anxiety (or generalized anxiety disorder), neuropathic pain, or peripheral diabetic neuropathic pain) in a human patient who is consuming alcohol, comprising administering, once a day or twice a day, a dosage form to a human patient in need thereof, and minimizing but not discontinuing consumption of alcohol by the human patient, wherein the dosage form comprises 105 mg of bupropion hydrochloride, or a molar equivalent amount of another salt form of bupropion or the free base form of bupropion, 45 mg of dextromethorphan hydrobromide, or a molar equivalent amount of another salt form of dextromethorphan or the free base form of dextromethorphan, and a polymer.

Some embodiments include a method of treating major depressive disorder in an adult human patient who is consuming alcohol, comprising administering, once a day or twice a day, a dosage form to a human patient in need thereof, wherein the dosage form comprises 105 mg of bupropion hydrochloride, or a molar equivalent amount of another salt form of bupropion or the free base form of bupropion, 45 mg of dextromethorphan hydrobromide, or a molar equivalent amount of another salt form of dextromethorphan or the free base form of dextromethorphan, and a polymer; wherein if the human patient is a male, the human patient is consuming two servings or less of alcohol per day; and if the human patient is a female, the human patient is consuming one serving or less of alcohol per day.

Some embodiments include a method of treating major depressive disorder comprising, administering a dosage form described herein to a human being in need thereof. In some embodiments, the dosage form is taken with an alcoholic beverage. In some embodiments, the dosage form is taken with a high-fat meal.

Some embodiments include a method of treating agitation associated with Alzheimer's disease in a human patient having agitation associated with Alzheimer's disease comprising: 1) orally administering a first dosage form once daily for one week to the human patient, then administering the first dosage form twice daily to the human patient for one week; and 2) then orally administering a second dosage form twice daily to the human patient for at least one week; wherein the human patient has agitation associated with dementia due to Alzheimer's disease, and is not using a selective serotonin reuptake inhibitor (SSRI) or a serotonin; wherein the first dosage form comprises about 30 mg of dextromethorphan hydrobromide, or a molar equivalent amount of another salt form of dextromethorphan or the free base form of dextromethorphan, about 105 mg of bupropion hydrochloride, or a molar equivalent amount of another salt form of bupropion or the free base form of bupropion, and a polymer; wherein the second dosage form comprises about 45 mg of dextromethorphan hydrobromide, or a molar equivalent amount of another salt form of dextromethorphan or the free base form of dextromethorphan, and about 105 mg of bupropion hydrochloride, or a molar equivalent amount of another salt form of bupropion or the free base form of bupropion; wherein the first and second dosage forms are bilayer tablets, and wherein the bupropion and the dextromethorphan in each of the tablets are in separate layers.

DETAILED DESCRIPTION

Figure 1:
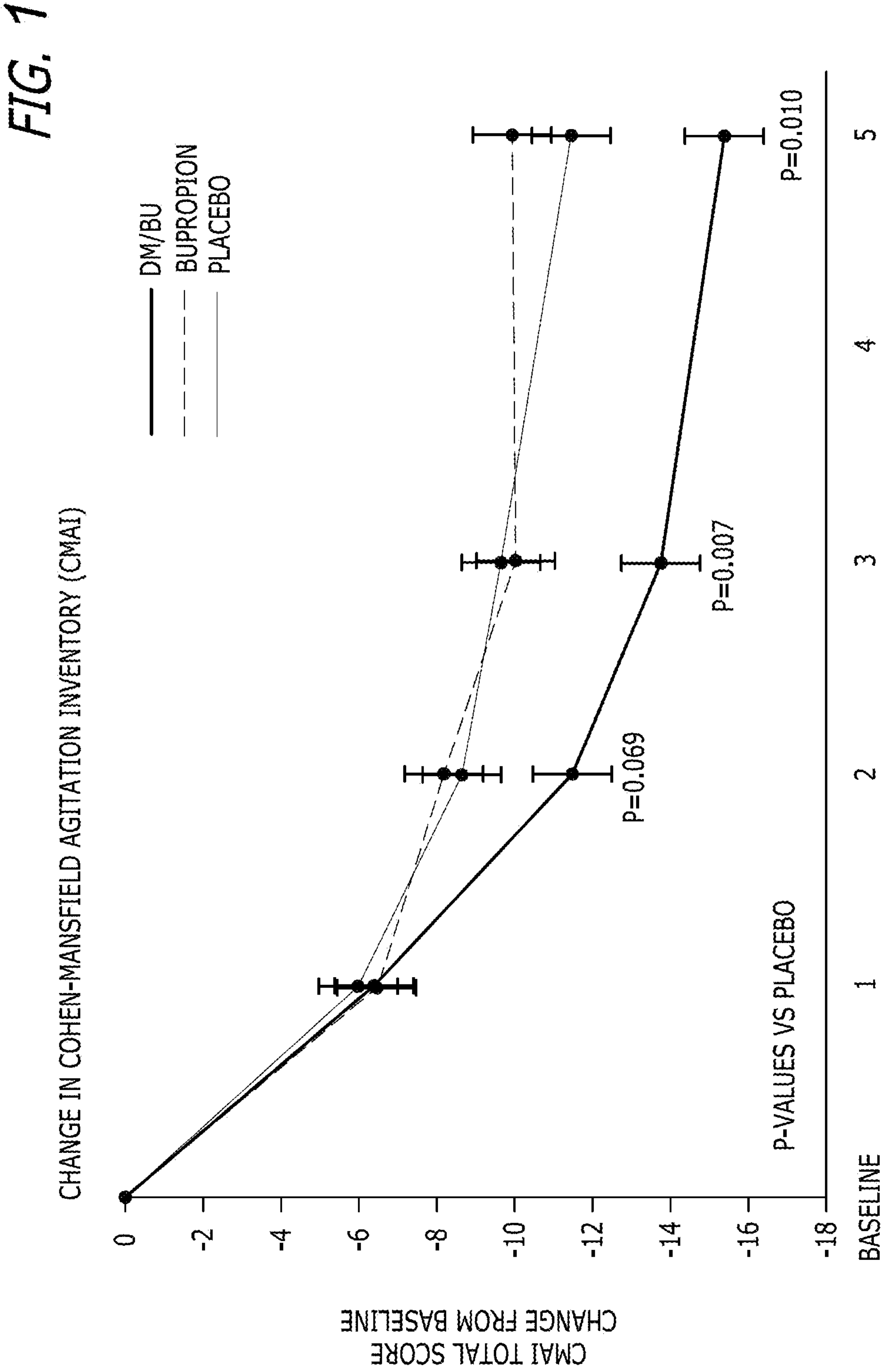
FIG. 1 is a plot of the CMAI total score change from baseline over time for the subjects described in Example 3.

Dose dumping is a phenomenon in which relatively a large amount of drug in a controlled release formulation is quickly released and a potentially toxic quantity of the drug is introduced into systemic circulation.

A pharmaceutical composition or dosage form described herein may include, or be prepared from, any suitable form of bupropion, such as a salt form, e.g., bupropion hydrochloride, the free base form, hydrates, solvates, polymorphs, other solid forms, etc. In some embodiments, the pharmaceutical composition is free of any other active pharmaceutical agents.

The pharmaceutical dosage form may include any suitable amount of bupropion, such as about 90-100 mg, about 100-110 mg, about 110-120 mg, about 103-107 mg, or about 105 mg of the bupropion, such as bupropion hydrochloride, a molar equivalent amount of another salt form of bupropion, or the free base form of bupropion.

The chemical name of bupropion hydrochloride is: (±)-1-(3-chlorophenyl)-2-[(1,1-dimethylethyl)amino]-1-propanone hydrochloride. Bupropion hydrochloride has the empirical formula $C_{13}H_{18}ClNO \cdot HCl$ and a molecular weight of 276.2 (239.74 bupropion base). The structural formula is:

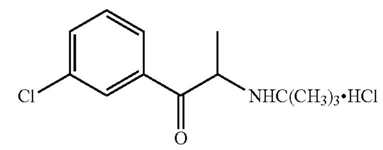

Bupropion hydrochloride powder is white and highly soluble in water.

A pharmaceutical composition or dosage form described herein may include, or be prepared from, any suitable form of dextromethorphan, such as a salt form, e.g., dextromethorphan hydrobromide, the free base form, hydrates, solvates, polymorphs, other solid forms, etc. In some embodiments, the pharmaceutical composition is free of any other active pharmaceutical agents.

The pharmaceutical dosage form may include any suitable amount of dextromethorphan, such as about 30-60 mg, about 30-50 mg, about 30-34 mg, about 34-38 mg, about 38-42 mg, about 42-46 mg, about 46-50 mg, about 40-45 mg, about 45-50 mg, about 44-46 mg, or about 45 mg of the dextromethorphan, such as bupropion hydrochloride, a molar equivalent amount of another salt form of dextromethorphan, or the free base form of dextromethorphan.

The chemical name of dextromethorphan hydrobromide is morphinan, 3-methoxy-17-methyl-,(9α,13α,14α), hydrobromide monohydrate. Dextromethorphan hydrobromide has the empirical formula $C_{18}H_{25}NO \cdot HBr \cdot H_2O$ and a molecular weight of 370.33 (271.4 dextromethorphan base). The structural formula is:

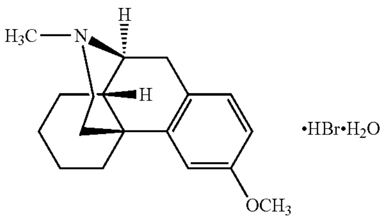

Dextromethorphan hydrobromide powder is white or almost white, crystalline, and sparingly soluble in water.

In some embodiments, the dosage form may contain bupropion and dextromethorphan, and no other active pharmaceutical ingredients. In some embodiments, the bupropion and the dextromethorphan are in two different layers or phases of the dosage form, e.g., each layer contains only bupropion or dextromethorphan and none of the other.

The pharmaceutical composition or dosage form may include cysteine (e.g., L-cysteine), such as about 30-100 mg, or about 50-100 mg of the cysteine, such as L-cysteine hydrochloride, another salt form of L-cysteine, or the neutral or zwitterionic form of L-cysteine. Cysteine in these amounts may be helpful in stabilizing bupropion in the presence of other excipients.

The pharmaceutical composition or dosage form may further comprise a sustained release or controlled release polymer, such as a crosslinked or uncrosslinked acrylate polymer or copolymer (including a poly(acrylic acid) or a poly(alkacrylic acid), such as poly(methacrylic acid), e.g., a carbomer homopolymer Type A such as Carbopol 971P), a cellulose derivative, such as methylcellulose, etc. In some embodiments, the controlled release polymer (e.g., a carbomer copolymer Type A) is about 1-40%, about 1-5%, about 5-10%, about 10-15%, about 15-20%, about 20-30%, about 30-40%, about 11-13%, or about 12% of the weight of the pharmaceutical composition. In some embodiments, the controlled release polymer is about 0.1-20%, about 0.1-2%, about 2-4%, about 4-6%, about 6-8%, about 8-10%, about 10-15%, about 15-20%, or about 7% of the weight of the dosage form.

The pharmaceutical composition or dosage form may further comprise a filler such as microcrystalline cellulose. In some embodiments, the filler may be about 20-60%, about 20-30%, about 30-40%, about 40-50%, or about 50-60% of the weight of the pharmaceutical composition or the dosage form.

The pharmaceutical composition or dosage form may further comprise a lubricant such as magnesium stearate. In some embodiments, the lubricant is about 0.1-10%, about 0.1-2%, about 2-4%, about 4-6%, about 6-8%, or about 8-10% of the weight of the pharmaceutical composition or the dosage form.

The dosage form may be formulated for any suitable route of administration, such as oral administration.

Dosage forms, such as solid dosage forms, e.g. capsules, tablets, or pills, for oral administration may also contain one or more of the following: a binder such as gum tragacanth, acacia, corn starch, or gelatin; an excipient, such as dicalcium phosphate; a disintegrating agent such as corn starch, potato starch, alginic acid, and the like; a sweetening agent such as sucrose, lactose, or saccharin; or a flavoring agent such as peppermint, oil of wintergreen, or cherry flavoring. When the dosage form is a capsule, it may contain, in addition to materials of the above type, a liquid carrier. Various other materials may be present as a coating, for example, tablets, pills, or capsules may be coated with shellac, sugar, or both. It may be desirable for material in a dosage form or pharmaceutical composition to be pharmaceutically pure and nontoxic in the amounts employed.

In some embodiments, the dosage form contains cysteine, Carbopol 971P, microcrystalline cellulose, silicon dioxide, and magnesium. In some embodiments, the dosage form contains a first layer comprising bupropion and cysteine, and a second layer comprising dextromethorphan, microcrystalline cellulose, croscarmellose sodium, and magnesium stearate.

An example of a single layer dosage form is show below:

| Layer 1 | |
|---|---|
| Ingredient | Amount (mg) |
| Bupropion | 90-120 |
| Cysteine | 30-100 |
| Carbopol 971P | 20-60 |
| Microcrystalline Cellulose | 200-300 |
| Colloidal Silicon Dioxide | 1-10 |
| Magnesium Stearate | 1-10 |

A two layer dosage form may contain a first layer with the composition shown above (Layer 1), and a second layer detailed below (Layer 2).

| Layer 2 | |
|---|---|
| Ingredient | Amount (mg) |
| Dextromethorphan | 30-60 |
| Microcrystalline Cellulose | 100-150 |
| Croscarmellose sodium | 1-20 |
| Magnesium Stearate | 1-10 |

In some embodiments, the dosage form may be for oral administration and may be a round bilayer tablet. Each tablet may contain 45 mg dextromethorphan hydrobromide (equivalent to 32.98 mg dextromethorphan base) in an immediate-release formulation and 105 mg bupropion hydrochloride (equivalent to 91.14 mg bupropion base) in an extended-release formulation. Each tablet may further contain any, or all, of the following inactive ingredients: carbomer homopolymer, colloidal silicon dioxide, crospovidone, glyceryl monocaprylocaprate, I-cysteine hydrochloride monohydrate, magnesium stearate, microcrystalline cellulose, polyvinyl alcohol, red iron oxide, sodium lauryl sulfate, stearic acid, talc, titanium dioxide, and/or yellow iron oxide. The pharmaceutical compositions or dosage forms described herein may be useful in treating neurological disorders or psychiatric conditions, such as depression, including major depressive disorder or treatment-resistant major depressive disorder, agitation, such as agitation associated with Alzheimer's disease, addiction, such as nicotine addiction, etc. For example, the pharmaceutical composition of dosage form may be administered once or twice a day to a human being suffering from a neurological disorder or psychiatric condition. Treatment may be continued as needed while the treatment is effective and safe, e.g., for at least 1 week, at least 4 weeks, at least one month, at least 2 months, at least 3 months, at least 6 months, at least 1 year, 1 week to 2 months, 1-3 months, 3-6 months, 6-12 months, 1-2 years, or possibly longer.

Due to US Food and Drug Administration (FDA) concern of dose dumping of bupropion hydrochloride when taken with ethanol, the FDA currently requests that dissolution testing on dosage forms containing bupropion be conducted using various concentrations of ethanol in the dissolution medium, as follows:

Testing Conditions: 900 mL, 0.1 N HCl, USP apparatus 2 (paddle) at 50 rpm, with or without ethanol;

Test 1:12 units tested according to the proposed method (with 0.1N HCl), with data collected every 15 minutes for a total of 2 hours;

Test 2:12 units analyzed by substituting 5% (v/v) of test medium with Alcohol USP (ethanol) and data collection every 15 minutes for a total of 2 hours;

Test 3:12 units analyzed by substituting 20% (v/v) of test medium with Alcohol USP (ethanol) and data collection every 15 minutes for a total of 2 hours; and Test 4:12 units analyzed by substituting 40% (v/v) of test medium with Alcohol USP (ethanol) and data collection every 15 minutes for a total of 2 hours.

According to the FDA, both test and reference products must be tested accordingly, and data must be provided on individual unit, means, range and % CV on both strengths. (FDA Draft Guidance on Bupropion Hydrochloride, p. 2.)

Literature Examples

According to FDA documents the bupropion product Forfivo XL was tested for ethanol dose dumping. (Center for Drug Evaluation and Research, Application No. 022497Orig1s000), CLINICAL PHARMACOLOGY AND BIOPHARMACEUTICS REVIEW(S) ("Forfivo Resubmission"), p. 17.) The Forfivo Resubmission discloses that Forfivo contains bupropion hydrochloride, hydroxypropyl cellulose, hydrochloric acid, polyethylene oxide, stearic acid, colloidal silicon dioxide, magnesium stearate, methacrylic acid copolymer, talc, polyethylene glycol (PEG) 8000, titanium oxide ($TiO_2$), and carboxymethylcellulose sodium (NaCMC). (Forfivo Resubmission, p. 10). The Forfivo Resubmission further reports that experiment described above was conducted for BUP 450 XL tablets. According to the Forfivo Resubmission, "[f]or 2 hours, no dissolved bupropion HCl from BUP 450 XL tablets was seen at 0% of alcohol. In the presence of 20% of alcohol, 7% of dissolved bupropion HCl from BUP 450 XL tablets was observed in two hours. In the presence of 40% of alcohol, 22% (range of 16-25%) of dissolved bupropion HCl from BUP 450 XL tablets was seen in two hours. The drug product is showing dose dumping with alcohol in vitro." (p. 17)

According to the CONTRAVE label, when a dosage form containing 8 mg of naltrexone HCl, 90 mg of bupropion HCl, microcrystalline cellulose, hydroxypropyl cellulose, lactose anhydrous, L-cysteine hydrochloride, crospovidone, magnesium stearate, hypromellose, edetate disodium, lactose monohydrate, colloidal silicon dioxide, Opadry II Blue, and FD&C Blue #2 aluminum lake was administered with a high-fat meal, the AUC and $C_{max}$ for naltrexone increased 2.1-fold and 3.7-fold, respectively, and the AUC and $C_{max}$ for bupropion increased 1.4-fold and 1.8-fold, respectively. At steady state, the food effect increased AUC and $C_{max}$ for naltrexone by 1.7-fold and 1.9-fold, respectively, and increased AUC and $C_{max}$ for bupropion by 1.1-fold and 1.3-fold, respectively. Thus, the label indicates that CONTRAVE should not be taken with high-fat meals because of the resulting significant increases in bupropion and naltrexone systemic exposure.

The subject combination may be used for adjunctive treatment of major depressive disorder or depression.

In addition to major depressive disorder, the subject combination may be used to treat other diseases in conditions in the patient populations or circumstances described herein. For example, the subject combination may be used to treat pain or a neurological disorder. Examples of neurological disorders that may be treated with the subject combination include, but are not limited to: affective disorders, psychiatric disorders, cerebral function disorders, movement disorders, dementias, motor neuron diseases, neurodegenerative diseases, seizure disorders, and headaches.

Affective disorders that may be treated by the subject combination include, but are not limited to, depression, major depression, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts, or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Psychiatric disorders that may be treated by the subject combination, include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease. Alzheimer's disease may also be referred to as dementia of the Alzheimer's type. Other neurobehavioral symptoms of Alzheimer's disease that may be treated include disinhibition and apathy.

Agitation in Alzheimer's disease occurs as the disease progresses. Agitation may present itself as inappropriate verbal, emotional, and/or physical behaviors. Inappropriate behaviors may include, but are not limited to, incoherent babbling, inappropriate emotional response, demands for attention, threats, irritability, frustration, screaming, repetitive questions, mood swings, cursing, abusive language, physical outbursts, emotional distress, restlessness, shredding, sleeping disturbances, delusions, hallucinations, pacing, wandering, searching, rummaging, repetitive body motions, hoarding, shadowing, hitting, scratching, biting, combativeness, hyperactivity, and/or kicking.

Alzheimer's disease (AD) is a progressive neurodegenerative disorder characterized by cognitive decline, and behavioral and psychological symptoms including agitation. AD is the most common form of dementia and afflicts an estimated 6 million individuals in the United States, a number that is anticipated to increase to approximately 14 million by 2050. Agitation is reported in up to 70% of patients with AD and is characterized by emotional distress, aggressive behaviors, disruptive irritability, and disinhibition. Managing agitation is a priority in AD. Agitation in patients with AD has been associated with increased caregiver burden, decreased functioning, accelerated cognitive decline, earlier nursing home placement, and increased mortality. There are currently no therapies approved by the FDA for the treatment of agitation in patients with AD.

Neurobehavioral symptoms have been known to appear during dementia and may be treated by the combination.

Caregivers or families may feel more overwhelmed by patients' behavioral/psychological symptoms than by their cognitive impairment. Common forms of the syndrome are Alzheimer's disease, vascular dementia, dementia with Lewy bodies (abnormal aggregates of protein that develop inside nerve cells), and a group of diseases that contribute to frontotemporal dementia (degeneration of the frontal lobe of the brain). The symptoms that dementia patients have are similar to those of psychiatric disorders, but some are slightly different from each other. Neurobehavioral symptoms associated with dementia include depression, apathy, agitation, disinhibition, hallucinations, delusions, psychosis, impulsiveness, aggressiveness, compulsion, excessive sex drive, and personality disorders. Neurobehavioral symptoms such as disinhibition may also be found in other conditions such as traumatic brain injury.

Agitation in patients with Alzheimer's disease may be assessed using the Cohen Mansfield Agitation Inventory or CMAI. The CMAI assesses various behaviors including, Hitting (including self), Kicking, Grabbing onto people, Pushing, Throwing things, Biting, Scratching, Spitting, Hurting self or others, Tearing things or destroying property, Making physical sexual advances, Pacing, aimless wandering, Inappropriate dress or disrobing, Trying to get to a different place, Intentional falling, Eating/drinking inappropriate substances, Handling things inappropriately, Hiding things, Hoarding things, Performing repetitive mannerisms, General restlessness, Screaming, Making verbal sexual advances, Cursing or verbal aggression, Repetitive sentences or questions, Strange noises (weird laughter or crying), Complaining, Negativism, Constant unwarranted request for attention or help.

Schizophrenia may be treated by the combination including positive symptoms and/or negative symptoms of schizophrenia, or residual symptoms of schizophrenia. Other conditions that may treated include intermittent explosive disorder.

Cerebral function disorders that may be treated by the subject combination include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Substance addiction abuse that may be treated by the subject combination includes, but is not limited to, drug dependence, addiction to cocaine, psychostimulants (e.g., crack, cocaine, speed, meth), nicotine, alcohol, opioids, anxiolytic and hypnotic drugs, cannabis (marijuana), amphetamines, hallucinogens, phencyclidine, volatile solvents, and volatile nitrites. Nicotine addiction includes nicotine addiction of all known forms, such as smoking cigarettes, cigars and/or pipes, e-cigarettes or vaping, and addiction to chewing tobacco.

Movement disorders that may be treated by the subject combination include, but are not limited to, akathisia, akinesia, associated movements, athetosis, ataxia, ballismus, hemiballismus, bradykinesia, cerebral palsy, chorea, Huntington's disease, Huntington's disease chorea, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by the subject combination include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by the subject combination include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandhoff disease, and hereditary spastic paraplegia.

Neurodegenerative diseases that may be treated the subject combination include, but are not limited to, Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia.

Seizure disorders that may be treated by the subject combination include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by the subject combination include, but are not limited to, migraine, tension, and cluster headaches.

Other neurological disorders that may be treated by the subject combination include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, the subject combination may be used to treat pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

In some embodiments, the subject combination may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc.

In some embodiments, the subject combination may be administered to relieve inflammatory pain including musculoskeletal pain, arthritis pain, and complex regional pain syndrome.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, the subject combination is used to treat chronic musculoskeletal pain.

In some embodiments, the subject composition may be administered to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component. Complex regional pain syndrome is a debilitating pain syndrome. It is characterized by severe pain in a limb that can be accompanied by edema, and autonomic, motor, and sensory changes.

In some embodiments, the subject composition may be administered orally to relieve neuropathic pain.

Examples of neuropathic pain include pain due to diabetic peripheral neuropathy or diabetic peripheral neuropathic pain, post-herpetic neuralgia, trigeminal neuralgia, monoradiculopathies, phantom limb pain, central pain, pain due to multiple sclerosis, etc. Other causes of neuropathic pain include cancer-related pain, lumbar nerve root compression, spinal cord injury, post-stroke pain, central multiple sclerosis pain, HIV-associated neuropathy, and radio- or chemotherapy associated neuropathy, etc.

In some embodiments, the subject composition may be administered to relieve fibromyalgia.

The term "treating", or "treatment" includes the diagnosis, cure, mitigation, treatment, or prevention of disease in man or other animals, or any activity that otherwise affects the structure or any function of the body of man or other animals.

A subject combination may be used to treat any disease or condition identified as treatable by the combination of bupropion and dextromethorphan in any of the following U.S. Pat. Nos. 8,569,328, 9,168,234, 9,189,905 9,205,083, 9,238,032, 9,278,095, 9,314,462, 9,370,513, 9,375,429, 9,408,815, 9,421,176, 9,457,023, 9,457,025, 9,474,731, 9,486,450, 9,700,528, 9,700,553, 9,707,191, 9,763,932, 9,861,595, 9,867,819, 9,968,568, 10,058,518, 10,064,857, 10,080,727, 10,092,560, 10,092,561, 10,105,327, 10,105,361, 10,251,879, 10,463,634, 10,512,643, 10,548,857, 10,596,167, 10,772,850, 10,780,064, 10,780,066, 10,786,469, 10,786,496, 10,799,497, 10,806,710, 10,864,209, 10,874,663, 10,874,664, 10,874,665, 10,881,624, 10,881,657, 10,894,046, 10,894,047, 10,898,453, all of which are incorporated by reference herein in their entireties for their disclosure of diseases that may be treated by a combination of bupropion and dextromethorphan, including specific embodiments and combinations described therein.

As illustrated in the examples below, the subject combination has no dose dumping of bupropion in the presence of ethanol in vitro. As a result, patients may use alcohol as long as the use is minimized or limited. For example, an adult female may consume one serving of alcohol or less per day (such as one serving per day, 4 servings per week or less, 3 servings per week or less, 1 serving per week or less, 1 serving per month or less, 1 serving per year or less, etc.) or an adult male may consume two servings of alcohol or less per day (such as two servings per day, one serving per day, 4 servings per week or less, 3 servings per week or less, 1 serving per week or less, 1 serving per month or less, 1 serving per year or less, etc.).

Example 1

A two-layer dosage form having Layer 1 and Layer 2 as described above, was tested for ethanol dose dumping as described above. No dose dumping of bupropion in the presence of ethanol in vitro was observed.

Example 2

A two-layer dosage form having Layer 1 and Layer 2 as described above, was tested for a food effect by administering the dosage form with a high-fat meal to human subjects, and comparing the AUC and $C_{max}$ to that obtained when administered to fasted human subjects. No significant difference between the two groups was observed in either the AUC or the $C_{max}$ of bupropion or dextromethorphan.

U.S. Provisional Patent Application No. 63/370,771, filed Aug. 8, 2022, is incorporated by reference herein in its entirety.

Example 3

A Phase 2/3 randomized, double-blind, controlled, multicenter, U.S. clinical trial was conducted to evaluate the efficacy and safety of DM/BU in patients with agitation associated with Alzheimer's disease. A total of 366 patients with a diagnosis of probable Alzheimer's disease and clinically meaningful agitation associated with their disease were randomized, initially in a 1:1:1 ratio, to receive DM/BU (dextromethorphan/bupropion, dose escalated from 30 mg/105 mg once daily in the first week, to 30 mg/105 mg twice daily in the second week, to 45 mg/105 mg twice daily thereafter), bupropion (dose escalated from 105 mg once daily in the first week to 105 mg twice daily thereafter), or matching placebo, for 5 weeks. An independent data monitoring committee performed an interim futility analysis and recommended no further randomization to the bupropion arm. Subsequently, patients were randomized in a 1:1 ratio to receive DM/BU or placebo. Total patients randomized were 159, 49, and 158 to the DM/BU, bupropion, and placebo arms, respectively. The mean Cohen-Mansfield Agitation Inventory (CMAI) total scores at baseline were 60.8, 66.1, and 59.3, respectively for the DM/BU, bupropion, and placebo groups. The minimum score on the CMAI is 29, corresponding to the total absence of symptoms, with higher scores corresponding to greater agitation. The primary endpoint of the study was the change from baseline in the CMAI total score at Week 5. P-values were calculated based on least square mean estimates.

Inclusion criteria included male or female 65-90 years of age, diagnosis of probable Alzheimer's disease, according to the 2011 NIA-AA criteria, diagnosis of agitation, according to the IPA provisional definition of agitation, MMSE score between 10 and 24, an NPI-AA score ≥4, and community dwelling. Exclusion criterial included dementia of non-Alzheimer's type and current use of a selective serotonin reuptake inhibitor and/or a serotonin and norepinephrine inhibitor (SSRI/SNRI). Demographics and baseline characteristics are shown in Table 1 below.

TABLE 1

Demographics and Baseline Characteristics

| | DM/BU (n = 152) | Bupropion (n = 49) | Placebo (n = 156) |
|---|---|---|---|
| Age (years) | 75.2 (5.71) | 76.4 (6.13) | 75.1 (5.96) |
| Female Gender, n (%) | 86 (56.6%) | 22 (44.9%) | 91 (58.3%) |
| Race, n (%) | | | |
| White | 136 (89.5%) | 43 (87.8%) | 128 (82.1%) |
| Black or African American | 11 (7.2%) | 5 (10.2%) | 25 (16.0%) |
| Asian | 1 (0.7%) | 0 | 1 (0.6%) |
| Other or Not Reported | 4 (2.6%) | 1 (2.0%) | 2 (1.3%) |
| CMAI Score | 60.7 (17.40) | 66.1 (19.65) | 59.4 (15.60) |
| CGI-S (agitation) | 4.2 (0.77) | 4.4 (0.82) | 4.2 (0.65) |
| NPI-A/A Score | 7.2 (2.17) | 6.9 (2.45) | 6.8 (2.07) |
| MMSE | 18.7 (3.76) | 17.8 (4.19) | 18.8 (3.70) |

mITT population. Data are mean (SD) unless otherwise stated.
Abbreviations:
BMI = Body Mass Index;
BU = bupropion;
CGI-S = Clinical Global Impression - Severity;
CMAI = Cohen-Mansfield Agitation Inventory;
DM = dextromethorphan;
mITT = modified intent to treat;
MMSE = Mini-mental state examination;
NPI-A/A = Neuropsychiatric Inventory - Agitation and Aggressive domain.

As shown in FIG. 1, DM/BU met the primary endpoint by demonstrating a statistically significant mean reduction in the Cohen Mansfield Agitation Inventory (CMAI) total score compared to placebo at Week 5, with mean reductions from baseline of 15.4 points for DM/BU (n=152), 10.0 for BU 9n=49), and 11.5 points for placebo (n=156) (p=0.010).

Figure 2:
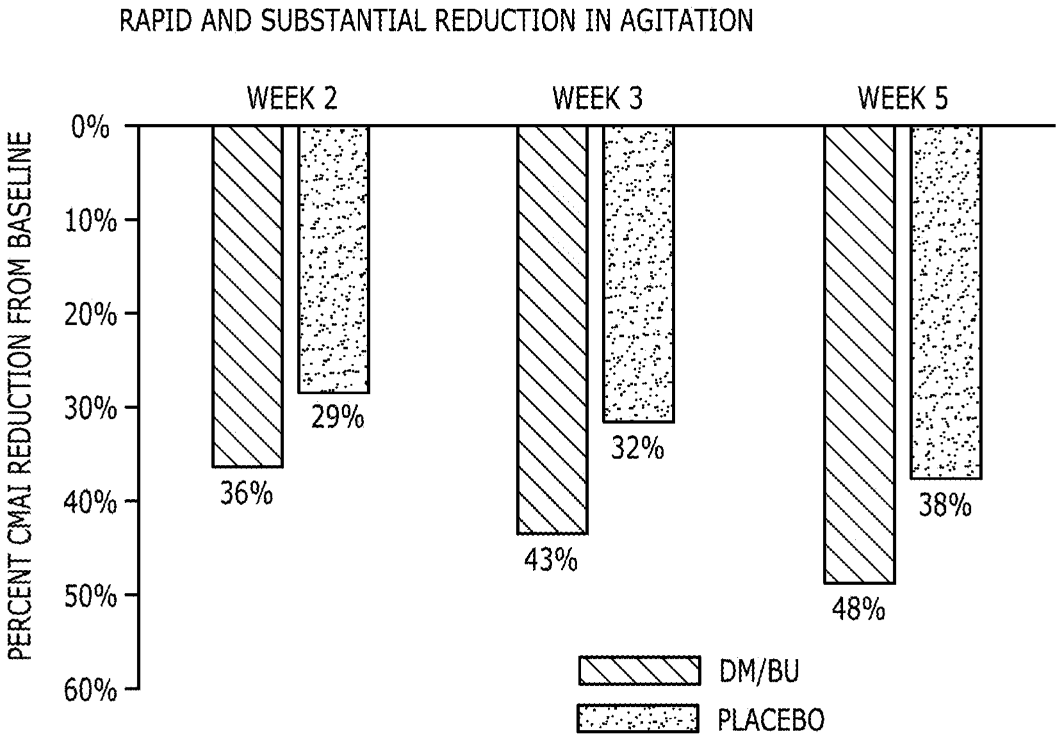
FIG. 2 is a plot of the percent CMAI reduction from baseline over time for the subjects described in Example 3.

As shown in FIG. 2, These results represent a mean percentage reduction of CMAI from baseline of 48% for DM/BU versus 38% for placebo. The CMAI is a 29-item caregiver-rated scale that assesses the frequency of agitation-related behaviors in patients with dementia, including excessive motor activity such as pacing and restlessness, verbal aggression such as screaming and shouting, and physical aggression such as grabbing, pushing, and hitting. DM/BU was also statistically superior to bupropion on the CMAI total score (p<0.001) at week 5, demonstrating component contribution.

DM/BU rapidly improved agitation symptoms. DM/BU numerically separated from placebo at Week 2 with a mean reduction from baseline in the CMAI total score of 11.5 points for DM/BU compared to 8.7 points for placebo (p=0.069).

DM/BU demonstrated a statistically significant mean reduction from baseline in the CMAI total score of 13.8 points for DM/BU compared to 9.7 points for placebo at Week 3 (p=0.007), with statistical significance for this measure maintained thereafter.

Figure 3:
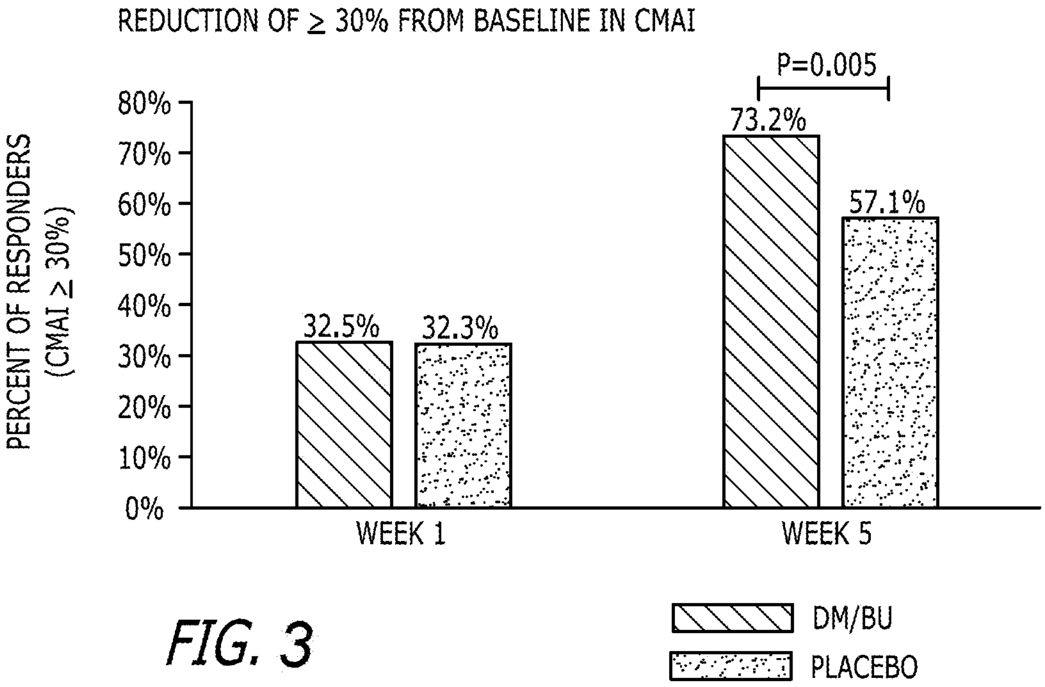
FIG. 3 is a plot of is a plot of the percentage of responders with CMAI reduction ≥30% from baseline over time for the subjects described in Example 3.

As shown in FIG. 3, a statistically significantly greater proportion of patients achieved a clinical response on the CMAI, defined as a 30% or greater improvement from baseline, with DM/BU as compared to placebo (73% versus 57%, p=0.005). These results were consistent with clinicians' global assessments of change measured using the modified Alzheimer's Disease Cooperative Study-Clinical Global Impression of Change for Agitation (mADCS-CGIC). DM/BU demonstrated statistically significantly greater improvement in agitation as compared to placebo on this measure (p=0.036).

DM/BU was safe and well tolerated in the trial. The most commonly reported adverse events in the DM/BU arm were somnolence (8.2% for DM/BU versus 4.1% for bupropion and 3.2% for placebo), dizziness (6.3%, 10.2%, 3.2%, for DM/BU, bupropion, and placebo arms respectively), and diarrhea (4.4%, 6.1%, 4.4%, for DM/BU, bupropion, and placebo arms respectively). The rates of discontinuation due to adverse events were 1.3%, 2.0%, and 1.3% in the DM/BU, bupropion, and placebo arms, respectively. Serious adverse events were reported in 3.1% of patients treated with DM/BU, compared to 8.2% of bupropion, and 5.7% of placebo-treated patients. No serious adverse events were deemed to be related to study drug in any treatment arm. There was one death in the placebo arm, one in the bupropion arm, and none in the DM/BU arm. There was no evidence of cognitive decline for patients treated with DM/BU as shown by the Mini-Mental State Examination (MMSE), a widely utilized measure of general cognitive function. Treatment with DM/BU was not associated with sedation. Adverse events are listed in Table 2 below.

TABLE 2

Treatment-Emergent Adverse Event

| | DM/BU (n = 159) | Bupropion (n = 49) | Placebo (n = 158) |
|---|---|---|---|
| Subjects with any TEAE | 70 (44.0%) | 30 (61.2%) | 52 (32.9%) |
| Somnolence | 13 (8.2%) | 2 (4.1%) | 5 (3.2%) |
| Dizziness | 10 (6.3%) | 5 (10.2%) | 5 (3.2%) |
| Diarrhea | 7 (4.4%) | 3 (6.1%) | 7 (4.4%) |
| Headache | 6 (3.8%) | 3 (6.1%) | 5 (2.5%) |
| Falls | 4 (2.5%) | 7 (14.3%) | 3 (1.9%) |
| Fatigue | 3 (1.9%) | 5 (10.2%) | 2 (1.3%) |
| Insomnia | 1 (0.6%) | 3 (6.1%) | 3 (1.9%) |
| Serious AEs | 5 (3.1%) | 4 (8.2%) | 9 (5.7%) |
| Discontinuation due to AEs | 2 (1.3%) | 1 (2.0%) | 2 (1.3%) |
| Deaths | 0 | 1 (2.0% | 1 (0.6%) |

Abbreviations:
AE = adverse event;
TEAE = Treatment-emergent adverse event.
Safety Population, data presented as number of subjects (% of subjects).
Treatment-emergent AEs occurring in >5% of subjects in any treatment group are presented.

Unless otherwise indicated, all numbers expressing quantities of ingredients, properties such as amounts, percentage, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Use of the term "comprising" or "comprises" herein also contemplates that use of "consisting essentially of," "consists essentially of," "consisting of," or "consists of" in its place.

Affirmative recitation of an element anywhere herein should be understood to contemplate both including and excluding that element.

The terms “a,” “an,” “the” and similar referents used in the context of describing the embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., “such as”) provided herein is intended merely to better illuminate the embodiments and does not pose a limitation on the scope of any claim. No language in the specification should be construed as indicating any non-claimed element essential to the practice of the claims.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from a group, for reasons of convenience and/or to expedite prosecution. When any such inclusion or deletion occurs, the specification is deemed to contain the group as modified thus fulfilling the written description of all Markush groups if used in the appended claims.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A method of treating agitation associated with Alzheimer’s disease in a human patient having agitation associated with Alzheimer’s disease comprising: 1) orally administering a first dosage form once daily for one week to the human patient, then administering the first dosage form twice daily to the human patient for one week; and 2) then orally administering a second dosage form twice daily to the human patient for at least one week; wherein the human patient has agitation associated with dementia due to Alzheimer’s disease, and is selected for not using a selective serotonin reuptake inhibitor (SSRI) or a serotonin;

wherein the first dosage form comprises about 30 mg of dextromethorphan hydrobromide, or a molar equivalent amount of another salt form of dextromethorphan or the free base form of dextromethorphan, about 105 mg of bupropion hydrochloride, or a molar equivalent amount of another salt form of bupropion or the free base form of bupropion, and a polymer;

wherein the second dosage form comprises about 45 mg of dextromethorphan hydrobromide, or a molar equivalent amount of another salt form of dextromethorphan or the free base form of dextromethorphan, and about 105 mg of bupropion hydrochloride, or a molar equivalent amount of another salt form of bupropion or the free base form of bupropion; and wherein the first and second dosage forms are bilayer tablets, and wherein the bupropion and the dextromethorphan in each of the tablets are in separate layers.

2. The method of claim 1, wherein the first or second dosage form further comprises colloidal silicon dioxide.

3. The method of claim 1, wherein the first or second dosage form further comprises crospovidone.

4. The method of claim 1, wherein the first or second dosage form further comprises glyceryl monocaprylocaprate.

5. The method of claim 1, wherein the first or second dosage form further comprises L-cysteine hydrochloride monohydrate.

6. The method of claim 1, wherein the first or second dosage form further comprises magnesium stearate.

7. The method of claim 1, wherein the first or second dosage form further comprises microcrystalline cellulose.

8. He method of claim 1, wherein the first or second dosage form further comprises polyvinyl alcohol.

9. The method of claim 1, wherein the first or second dosage form further comprises sodium lauryl sulfate.

10. The method of claim 1, wherein the first or second dosage form further comprises stearic acid.

11. The method of claim 1, wherein the first or second dosage form further comprises titanium dioxide.

12. The method of claim 1, wherein the polymer is a carbomer homopolymer.

13. The method of claim 1, wherein the first or second dosage form further comprises: colloidal silicon dioxide, crospovidone, glyceryl monocaprylocaprate, L-cysteine hydrochloride monohydrate, magnesium stearate, microcrystalline cellulose, polyvinyl alcohol, red iron oxide, sodium lauryl sulfate, stearic acid, talc, titanium dioxide, or yellow iron oxide, or a combination thereof.

14. The method of claim 1, wherein the first or second dosage form comprises about 105 mg of bupropion hydrochloride.

15. The method of claim 1, wherein the first dosage form comprises about 30 mg of dextromethorphan hydrobromide.

16. The method of claim 14, wherein the first dosage form comprises about 30 mg of dextromethorphan hydrobromide.

17. The method of claim 1, wherein the second dosage form comprises about 45 mg of dextromethorphan hydrobromide.

18. The method of claim 14, wherein the second dosage form comprises about 45 mg of dextromethorphan hydrobromide.

19. The method of claim 1, wherein the dextromethorphan is formulated for immediate release.

20. The method of claim 19, wherein the bupropion is formulated for extended release.

* * * * *